US008882762B2

(12) United States Patent
Wang et al.

(10) Patent No.: US 8,882,762 B2
(45) Date of Patent: Nov. 11, 2014

(54) TRANSMURAL ABLATION DEVICE

(75) Inventors: Paul J Wang, Saratoga, CA (US); Amin Al-Ahmad, Cupertino, CA (US); William Francis Johnston, Sunnyvale, CA (US); Kai Ihnken, Arlington, VA (US); Kaartiga Sivanesan, Winter Springs, FL (US); Morgan Clyburn, Menlo Park, CA (US); Kathleen Lee Kang, Sunnyvale, CA (US); Lauren Shui Sum Chan, San Francisco, CA (US); Robert C Robbins, Stanford, CA (US); Friedrich B. Prinz, Woodside, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 367 days.

(21) Appl. No.: 13/512,493

(22) PCT Filed: Nov. 30, 2010

(86) PCT No.: PCT/US2010/003072
§ 371 (c)(1),
(2), (4) Date: May 29, 2012

(87) PCT Pub. No.: WO2011/065983
PCT Pub. Date: Jun. 3, 2011

(65) Prior Publication Data
US 2013/0131665 A1 May 23, 2013

Related U.S. Application Data

(60) Provisional application No. 61/264,874, filed on Nov. 30, 2009.

(51) Int. Cl.
*A61B 18/18* (2006.01)
*A61N 2/00* (2006.01)
*A61B 18/14* (2006.01)
*A61B 17/00* (2006.01)
*A61B 18/00* (2006.01)
*A61B 19/00* (2006.01)

(52) U.S. Cl.
CPC ............ *A61B 18/1492* (2013.01); *A61B 18/14* (2013.01); *A61B 2017/00876* (2013.01); *A61B 2018/00005* (2013.01); *A61B 2018/00291* (2013.01); *A61B 2018/00363* (2013.01); *A61B 2018/00577* (2013.01); *A61B 2019/2253* (2013.01)
USPC ............................................... 606/41; 600/10

(58) Field of Classification Search
CPC ............... A61B 18/14; A61B 18/1492; A61B 18/1442; A61B 2019/2253
USPC .............. 606/32–50; 607/103–105, 115–116; 600/10
See application file for complete search history.

(56) References Cited

U.S. PATENT DOCUMENTS

| 8,430,875 | B2* | 4/2013 | Ibrahim et al. | 606/41 |
| 2005/0187545 | A1* | 8/2005 | Hooven et al. | 606/41 |
| 2009/0124847 | A1* | 5/2009 | Doty et al. | 600/10 |
| 2010/0004661 | A1* | 1/2010 | Verin et al. | 606/129 |

* cited by examiner

Primary Examiner — Catherine Voorhees
(74) Attorney, Agent, or Firm — Lumen Patent Firm

(57) ABSTRACT

A transmural ablation device is provided to achieve endocardial and epicardial ablation at the same site but directed from the inner and outer surfaces of the heart to create a transmural lesion. By ablating from both sides of the heart tissue, it is possible to increase the depth of the lesion created and to increase the likelihood of a transmural lesion. Embodiments pertain to techniques to align the endocardial and epicardial ablation elements and techniques to position and move the endocardial and epicardial ablation elements along a predefined linear, curvilinear, or circular path. The ability to bring the epicardial and endocardial elements more closely or firmly with the underlying tissue is important in creating optimal lesions. Magnetic force attracts the epicardial and endocardial elements.

3 Claims, 10 Drawing Sheets

TRANSMURAL ABLATION DEVICE

CROSS-REFERENCE TO RELATED APPLICATIONS

This application is a 371 of PCT Patent Application PCT/US2010/003072 filed Nov. 30, 2010, which claims the benefit of U.S. Provisional Application 61/264,874 filed Nov. 30, 2009.

STATEMENT OF GOVERNMENT SPONSORED SUPPORT

This invention was made with Government support under contract RR025742 awarded by National Institutes of Health. The Government has certain rights in this invention.

FIELD OF THE INVENTION

The present invention relates generally to ablation devices, systems and methods. More particularly, the invention relates to transmural tissue ablation.

BACKGROUND OF THE INVENTION

Catheter ablation is a technique to treat cardiac arrhythmias by creating cell damage. Most forms of catheter ablation for arrhythmias are performed by delivering energy from the endocardial surface of the heart. Only a small proportion of ablation procedures are performed from the epicardial surface of the heart. Surgical ablation of arrhythmias may be performed endocardially and epicardially, but only epicardial ablation may be performed without cardiopulmonary bypass.

While epicardial ablation may be successful in some regions of the heart, in many cases, transmural lesions may be difficult to achieve using an epicardial approach alone. Current approaches to epicardial and endocardial ablation have limitations. One limitation relates to the difficulty with catheter positioning and achieving adequate contact from the endocardial surface that may limit the precision and ease of mapping (obtaining electrical signals from the heart that may identify the site of ablation) and the creation of adequate ablation lesions. Another limitation relates to the tachycardia focus that may require transmural lesions which may be difficult to achieve from either the endocardial or epicardial surface of the heart alone. Yet another limitation relates to some arrhythmias that may require mapping and ablation from both the endocardial and epicardial surfaces and one approach alone is insufficient. Still another limitation relates to the fact that obtaining 2 separate maps of the endocardial and epicardium is time consuming and does not permit one to align the endocardial lesions to create a transmural lesion. The present invention addresses at least one of the limitations and advances the art of endocardial and epicardial ablation by providing a transmural ablation device.

SUMMARY OF THE INVENTION

A transmural ablation device to create a transmural (full-thickness) lesion of a tissue is provided. The device distinguishes a leading electrode assembly and a following electrode assembly. In case of a cardiac ablation application, the leading electrode assembly functions at the epicardial site, while the following electrode assembly functions at the endocardial site.

The leading electrode assembly has a first electrode and a flexible elongated traveling structure, which can be adopted to a (predefined) linear, curvilinear or circular traveling path shape. The traveling structure is configured for the first electrode to travel along its longitudinal axis. At least part of the first electrode acts as a magnet. The leading electrode assembly could include an electrode array to map electrical activity of the tissue.

The following electrode assembly has a housing to support at one end a rolling ball. The housing is configured to allow the rolling ball to roll freely (360 degrees) within the housing. The rolling ball distinguishes an outer layer and an inner structure. The outer layer is a non-magnetic layer and the inner structure is a paramagnetic structure. The outer layer of the rolling ball and/or at least a part of the housing act as a second electrode. The following electrode assembly could include a cooling mechanism.

The leading electrode assembly is positioned at one side of a tissue surface and the following electrode assembly is positioned at the other side of the tissue surface. The magnetic force of the first electrode attracts the rolling ball through the tissue surface. Furthermore, the magnetic force enables rolling motion of the rolling ball along its respective tissue surface when the first electrode is traveling over its flexible elongated traveling structure and along its respective tissue surface.

The first electrode and the second electrode are configured to ablate and create a transmural lesion of the tissue when the first electrode and the second electrode face each other and sandwich the tissue through the magnetic attraction force.

A control system could be added to monitor and modify the strength of the magnetic field of the magnetic part of the first electrode.

DETAILED DESCRIPTION

Figure 1:
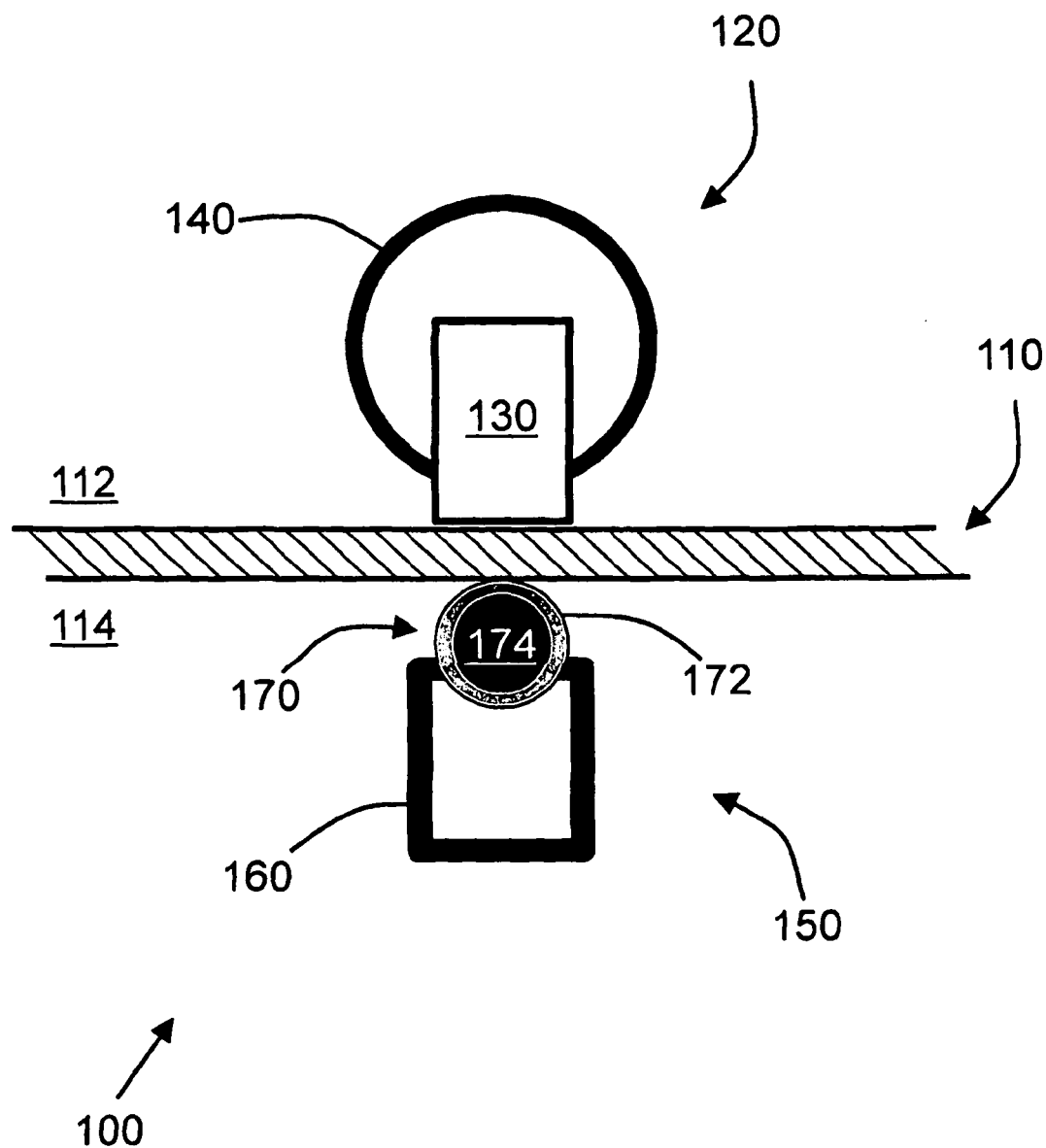
FIG. 1 shows an example of a frontal view 100 of a transmural ablation device according to an exemplary embodiment of the invention.

The basic concept of the invention is to achieve endocardial and epicardial ablation at the same site but directed from the inner and outer surfaces of the heart to create a transmural (full-thickness) lesion. By ablating from both sides of the heart tissue, it is possible to increase the depth of the lesion created and to increase the likelihood of a transmural lesion. Embodiments of the invention pertain to techniques to align the endocardial and epicardial ablation elements and techniques to position and move the endocardial and epicardial ablation elements along a predefined linear, curvilinear, or circular path. The ability to bring the epicardial and endocardial elements more closely or firmly with the underlying tissue is important in creating optimal lesions. Magnetic force attracts the epicardial and endocardial elements.

A transmural ablation device to create a transmural lesion of a tissue 110 includes a leading electrode assembly, which typically is at the epicardial site 112, and a following electrode assembly, which typically is at the endocardial site 114.

The leading electrode assembly contains a first electrode and a flexible elongated traveling structure. The traveling structure is configured such that the first electrode can travel along its longitudinal axis. At least part of the first electrode is a magnet.

The following electrode assembly contains a housing to support at one end a rolling ball. The housing is configured to allow the rolling ball to roll freely (i.e. 360 degrees) within the housing. The rolling ball distinguishes an outer layer and an inner structure. The outer layer is a non-magnetic layer and the inner structure is a paramagnetic (ball) structure. In one embodiment the outer layer of said rolling ball acts as the second electrode. In another embodiment at least a part of the housing adjacent to the rolling ball acts as a second electrode.

The rolling ball is capable of rolling along the surface of the tissue (e.g. direction D2). The rolling motion is instigated and/or maintained by the magnetic (attraction) force of the magnet of the leading electrode assembly exerted onto the paramagnetic material inside the rolling ball, while the leading electrode assembly is moving (e.g. direction D1) along the path of the traveling structure along the tissue surface.

A transmural lesion can be created when the first electrode is facing the second electrode while both electrodes are sandwiching the tissue. Typically the leading electrode assembly is then in stationary position to allow proper alignment and contact (through magnetic attraction force) of both electrodes on either side of the tissue. Simultaneous or sequential ablation energy delivered through both electrodes could establish the transmural lesion.

A control system could be added to monitor and modify the strength of the magnetic field of the magnetic part of the first electrode. The force created by the epicardial (first electrode) magnet and the endocardial rolling ball varies with the distance between these components. In some cases the tissue between these components is particularly thick, increasing the distance between these two components. To attract the endocardial rolling ball, one may increase the magnet field strength of the epicardial (first electrode) magnet. Changing the field strength of the epicardial (first electrode) magnet may be achieved by moving the magnet closer or farther away, moving in one or more additional magnets, or using an electromagnet. A positioning system that estimates the distance between the epicardial and endocardial components may be used in a control system to adjust the field strength. The magnet field is increased in strength automatically based on the epicardial and endocardial component distances. The orientation of the magnetic field may be automatically altered as the epicardial magnet is moved.

FIG. 1 shows a transmural ablation device 100 according to an embodiment of the invention. The leading electrode assembly 120 contains a first electrode 130 and a flexible elongated tubular traveling structure 140. Traveling structure 140 is configured such that first electrode 130 can travel along its longitudinal axis. The first electrode 130 is also a magnet.

The following electrode assembly 150 contains a housing 160 to support at one end a rolling ball 170. Housing 160 is configured to allow rolling ball 170 to roll freely (i.e. 360 degrees) within housing 160. Rolling ball 170 distinguishes an outer layer 172 and an inner structure 174. Outer layer 172 is a non-magnetic layer and inner structure 174 is a paramagnetic structure. In one embodiment outer layer 172 of rolling ball 170 acts a the second electrode. In another embodiment at least a part of housing 160 adjacent to the rolling ball acts as a second electrode. The outer layer 172 and at least part of housing 160 may combine to form the second electrode.

Figure 2:
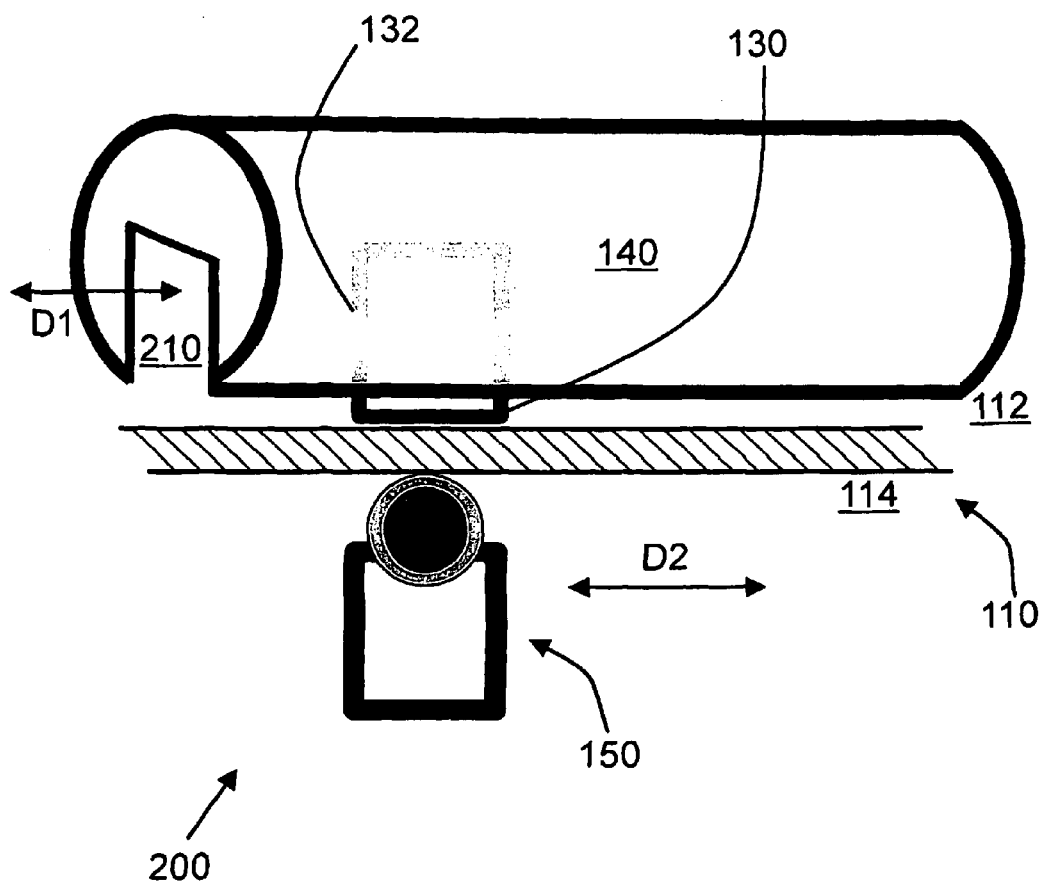
FIG. 2 shows an example of a side view 200 of the transmural ablation device according to the exemplary embodiment of FIG. 1.
Figure 3:
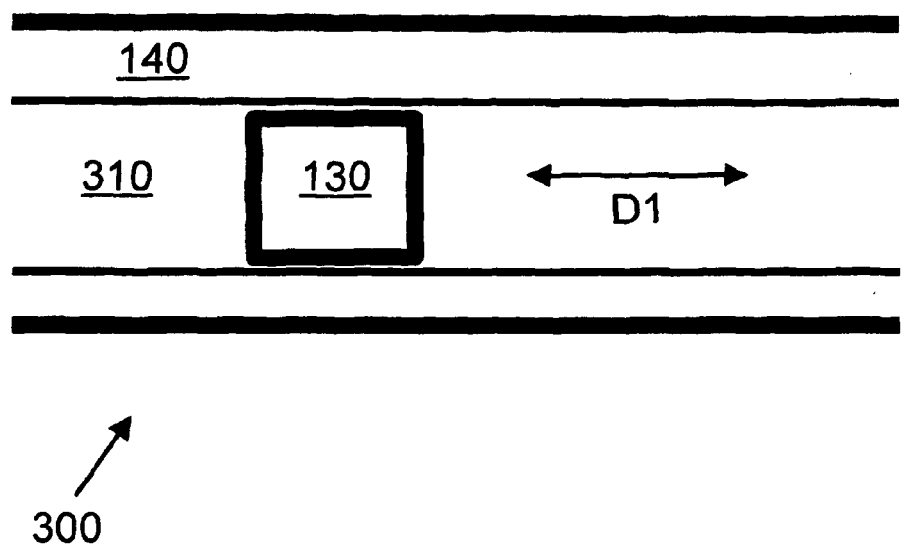
FIG. 3 shows an example of a bottom view 300 of the transmural ablation device according to the exemplary embodiment of FIG. 1.

The shape and size of first electrode 130 mates opening 210 of flexible elongated tubular traveling structure 140 (see side view FIG. 2). 130 is the part of first electrode extending outside the perimeter of structure 140 through the longitudinal surface slot 310 (see bottom view 300 in FIG. 3) of opening 210, and 132 is the part of first electrode inside the structure. First electrode 130 and the inside of structure 140 further have a rail or mechanism to ensure traveling of first electrode 130 within structure 140 and to avoid "derailing" of first electrode 130 with respect to structure 140. For example, grooves in structures 130 and 140 may be examples of elements to prevent derailing.

Figure 4:
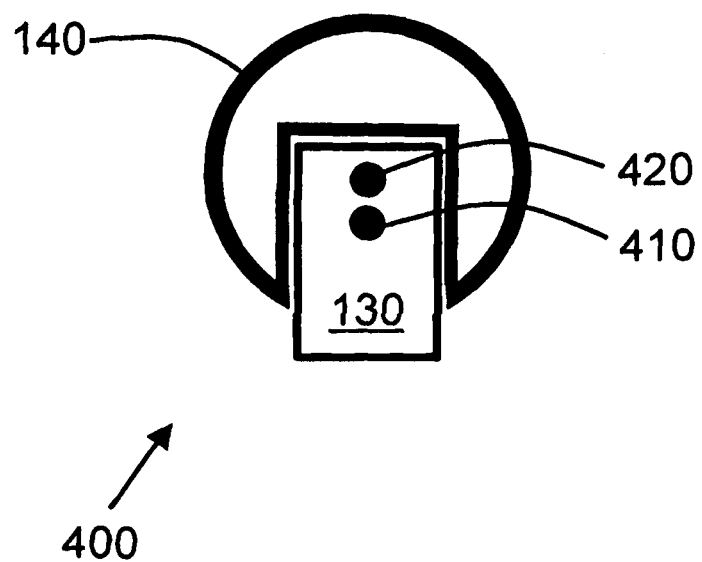
FIGS. 4-5 show examples of a leading electrode assembly 400, 500 according to exemplary embodiments of the invention.

FIG. 4 shows a frontal view of a leading electrode assembly 400 with flexible elongated tubular traveling structure 140 and first electrode 130. A pull wire 410 attached to first electrode 130 can be used to pull or push first electrode 130 within structure 140. A monorail wire 420 attached to first electrode 130 can be used to guide first electrode within structure 140.

Figure 5:
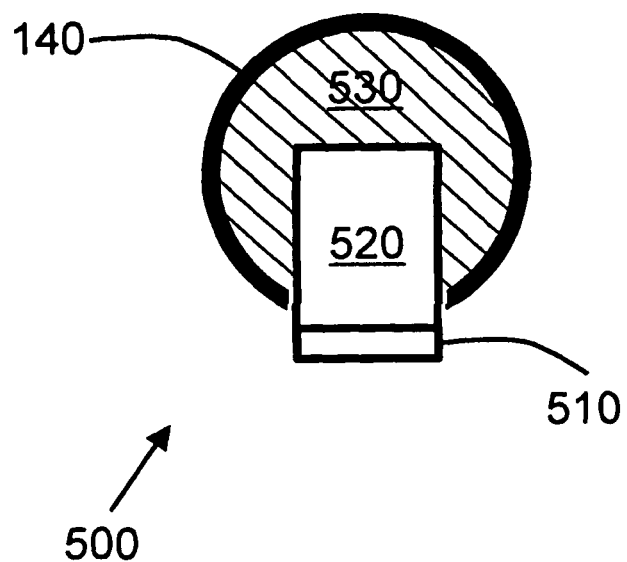

FIG. 5 shows a frontal view of a leading electrode assembly 500 with flexible elongated tubular traveling structure 140 and first electrode 510 layered over magnet 520. In this embodiment, the epicardial magnet does not act as the ablation element. The epicardial magnet has an overlaying non-paramagnetic material which serves as the electrode. A movable inner structure 530 attached to first electrode/magnet combination 510/520 is used to guide combination 510/520 within structure 140. In this embodiment there is no need for a separate guide wire.

Figure 6:
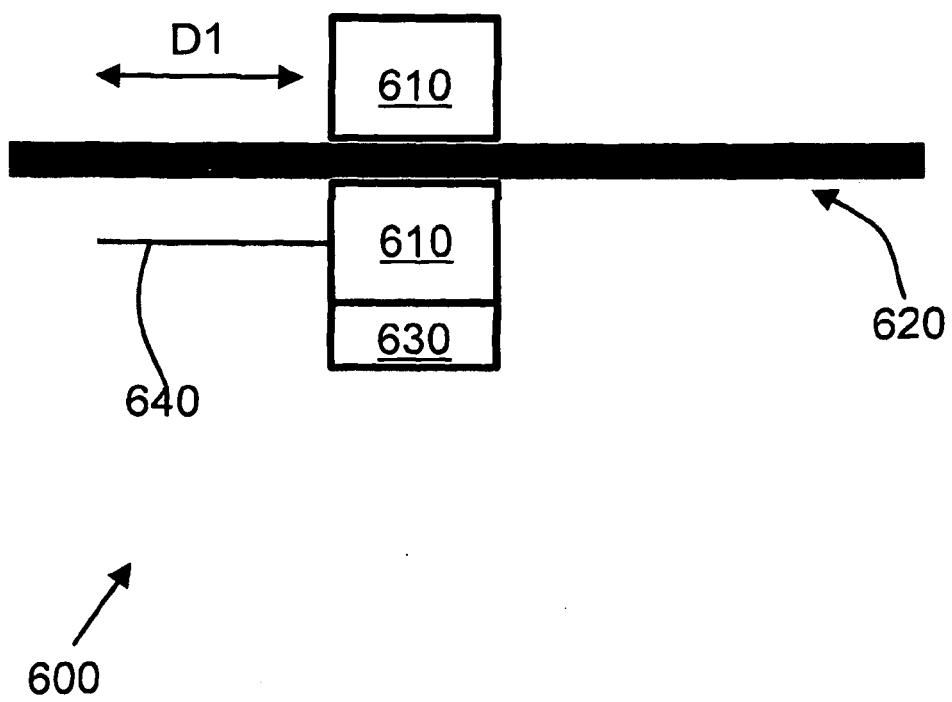
FIG. 6 shows an example of a side view 600 of a transmural ablation device according to an exemplary embodiment of the invention.
Figure 7:
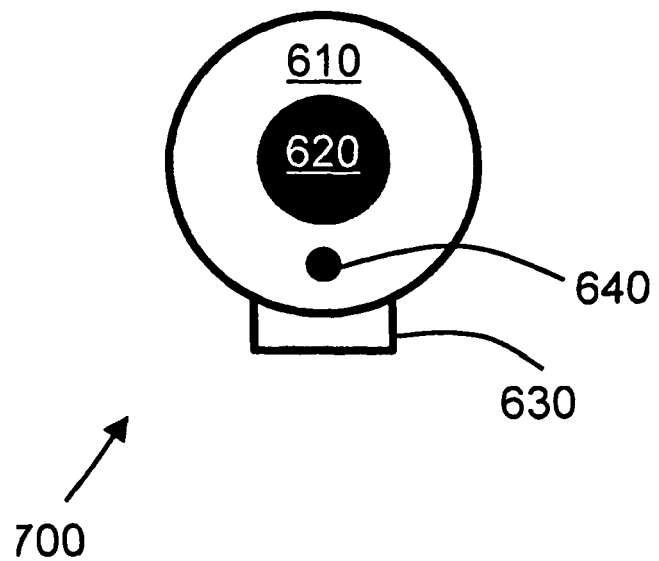
FIG. 7 shows an example of a frontal view 700 of the transmural ablation device according to the exemplary embodiment of FIG. 6.

FIG. 6 shows in a side view a leading electrode assembly 600 with a movable element 610 movable over a monorail or wire 620 with adequate stiffness that it can advance and retract first electrode 630. It is noted that first electrode 630 is attached to movable element 610 and together move over wire 620. In other words wire 620 acts as an inner track. Movement of first electrode 630 can e.g. be accomplished by pull wire 640. FIG. 7 shows a frontal view 700 of assembly 600 of FIG. 6.

Figure 8:
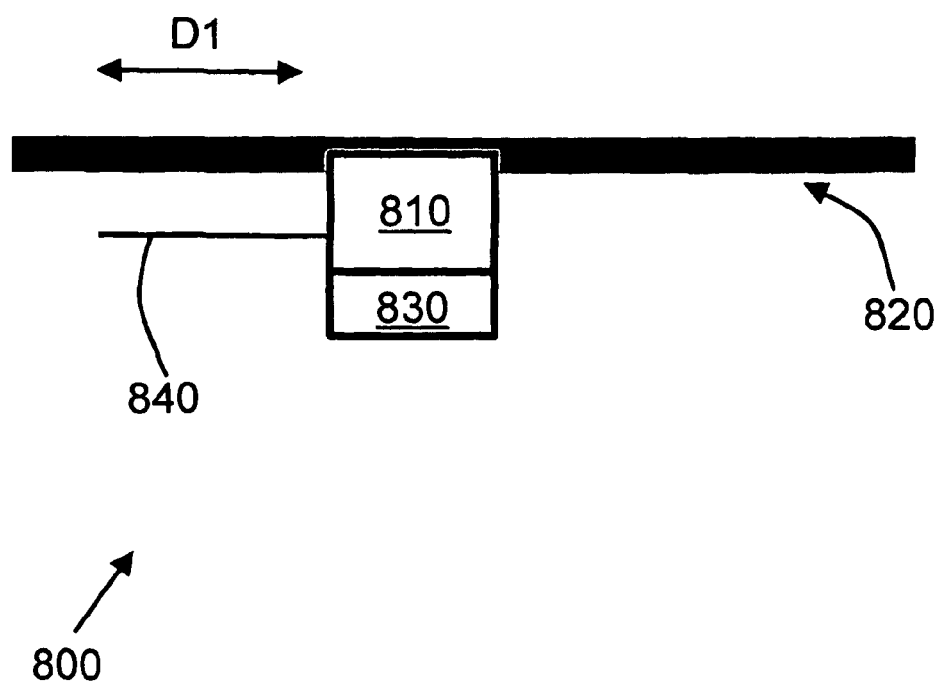
FIG. 8 shows another example of a side view 800 of a transmural ablation device according to an exemplary embodiment of the invention.
Figure 9:
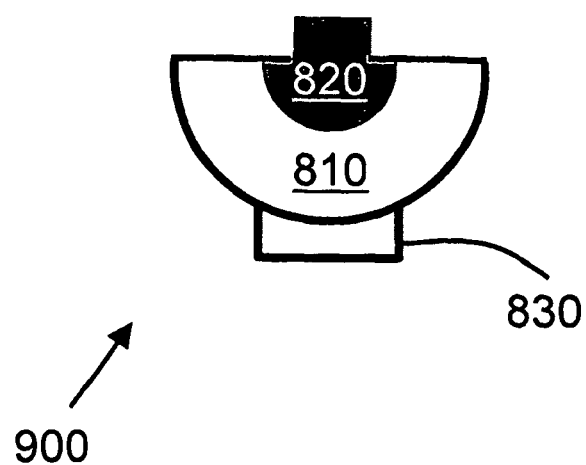
FIG. 9 shows an example of a frontal view 900 of the transmural ablation device according to the exemplary embodiment of FIG. 8.

FIG. 8 is an alternate embodiment of FIG. 6 and shows a side view of a leading electrode assembly 800 with a movable element 810 movable over a monorail 820 with adequate stiffness that it can advance and retract first electrode 830. It is noted that first electrode 830 is attached to movable element 810 and together move over monorail 820. Movement of first electrode 830 can e.g. be accomplished by pull wire 840. FIG. 9 shows a frontal view 900 of FIG. 8.

Figure 10:
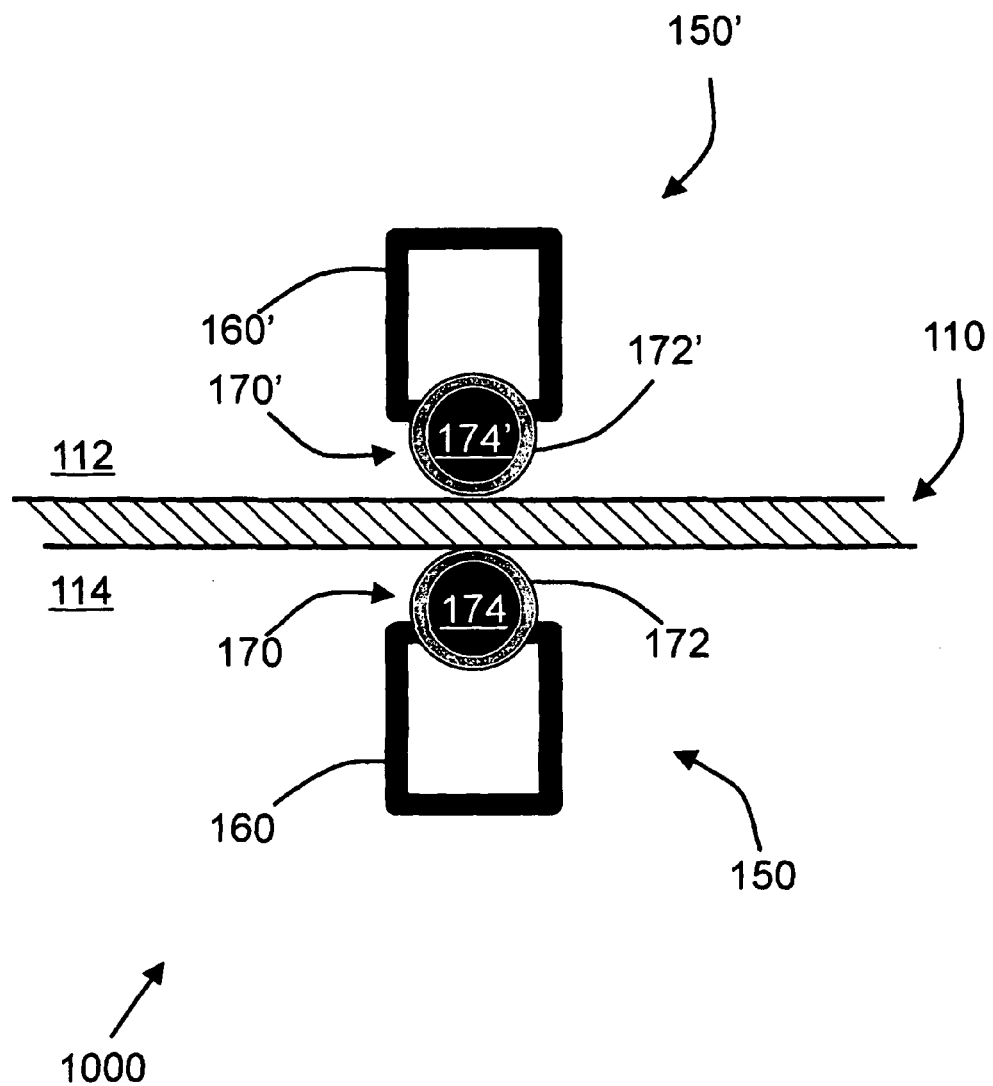
FIG. 10 shows an example of a frontal view 1000 of a transmural ablation device without a traveling structure according to an exemplary embodiment of the invention.

FIG. 10 is an alternate embodiment 1000 in which the leading electrode assembly 150' is similar to following electrode assembly 150 as discussed with respect to FIG. 1. The reference numbers for the elements are similar to each other with the difference of after the numeral. In this embodiment the traveling structure has been removed.

The endocardial device is introduced via the vascular system. For access to the left atrium, transseptal catheterization may be performed. In one variation, the epicardial device could be introduced via thoracoscopic elements into the chest. In another variation, the epicardial device is introduced via a thoracotomy. In yet another variation, epicardial access if obtained using a puncture needle in a sub-xiphoid position.

The invention has now been described in accordance with several exemplary embodiments, which are intended to be illustrative in all aspects, rather than restrictive. Thus, the present invention is capable of many variations in detailed implementation as device or method, which may be derived from the description contained herein by a person of ordinary skill in the art. In one variation, the leading electrode assembly could have suction elements to improve contact with the tissue surface. In another variation, in the embodiment of the monorail, a tube like guide may create a loop around an anatomic structure. The opening in the guide could then be oriented so that to contact of the electrode with the tissue is feasible.

In yet another variation, a loop catheter could be created in the endocardial site. A moveable paramagnetic or magnetic element may follow movement of an epicardial element that may or may not also be in a loop structure.

In still another variation, the tube or monorail could be placed around the pulmonary veins to achieve ablation that surrounds the pulmonary veins. This tube-like structure may be used to create a "box" lesion that results in isolation of the four pulmonary veins for the treatment of atrial fibrillation. The tube could be placed epicardially and pulled through the transverse and oblique sinuses so that the tube may wrap around the pulmonary veins. The epicardial electrode element may be pulled through the tube-like structure to create this ablation pattern.

Even though embodiments pertain to cardiac tissue, the invention can also be applied to other types of tissue, including different applications other than tissue ablation.

What is claimed is:

1. A transmural ablation device to create a transmural lesion of a tissue, comprising:
    a) a leading electrode assembly having a first electrode and a flexible elongated traveling structure configured for said first electrode to travel along the longitudinal axis of said flexible elongated traveling structure, and wherein at least part of said first electrode acts as a magnet; and
    b) a following electrode assembly, having a housing a rolling ball and to support at one end the rolling ball configured to roll freely within said housing, wherein said rolling ball comprises an outer layer and an inner structure, wherein said outer layer is a non-magnetic layer,
    wherein said inner structure is a paramagnetic structure, and wherein said outer layer of said rolling ball and/or at least a part of said housing act as a second electrode,
    wherein said leading electrode assembly is adapted to be located at one side of a tissue surface, wherein said following electrode assembly is adapted to be located at the other side of the tissue surface, wherein the magnetic force of said first electrode attracts said rolling ball through the tissue surface, wherein said magnetic force enables rolling motion of said rolling ball along its respective tissue surface when said first electrode is traveling over said flexible elongated traveling structure and along its respective tissue surface, and
    wherein said first electrode and said second electrode are configured to ablate and create said transmural lesion of the tissue when said first electrode and said second electrode face each other and sandwich the tissue through said magnetic force.

2. The transmural ablation device as set forth in claim 1, wherein said flexible elongated traveling structure adopts to a linear, curvilinear or circular traveling path shape.

3. The transmural ablation device as set forth in claim 1, further comprising a pull wire attached to said first electrode.

* * * * *